United States Patent [19]

Kathawala

[11] 4,011,232

[45] Mar. 8, 1977

[54] PHENOXYPHENYL PYRIDYL COMPOUNDS
[75] Inventor: Faizulla G. Kathawala, West Orange, N.J.
[73] Assignee: Sandoz, Inc., E. Hanover, N.J.
[22] Filed: Dec. 18, 1975
[21] Appl. No.: 635,681
[52] U.S. Cl. .............................. 260/297 R; 424/263
[51] Int. Cl.$^2$ ............. C07D 213/44; C07D 213/50
[58] Field of Search ................................ 260/297 R
[56] References Cited
UNITED STATES PATENTS 3,426,036  2/1969  Biel et al. ........................... 260/297
3,506,720  4/1970  Model et al. ....................... 260/613
3,891,661  6/1975  Sugisaka ........................... 260/297 R Primary Examiner—John D. Randolph
Attorney, Agent, or Firm—Gerald D. Sharkin; Richard E. Vila; Frederick H. Weinfeldt

[57] ABSTRACT

Phenoxyphenyl pyridyl carbinols and ketones, e.g., p-[4'-(2,2-dimethylpropyl)-phenoxy]-phenyl-(4-pyridyl)-carbinol, are useful as pharmaceutical agents. The ketones are obtainable by oxidation of corresponding phenoxyphenyl pyridyl carbinols.

18 Claims, No Drawings

PHENOXYPHENYL PYRIDYL COMPOUNDS

This invention relates to organic compounds, and more particularly to phenoxyphenyl pyridyl carbinols and ketones, and pharmaceutically acceptable acid addition salts thereof, and to pharmaceutical compositions containing such compounds, as well as to use of such compounds as pharmaceuticals.

The compounds of this invention are conveniently represented by the formula I:

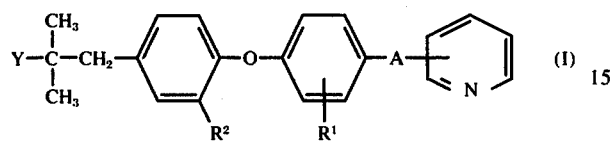

wherein

Y is unbranched alkyl having 1 to 3 carbon atoms,
each of $R^1$ and $R^2$ is, independently, a hydrogen atom, alkyl having from 1 to 4 carbons, or fluoro or chloro, i.e., a halogen atom having an atomic weight of from about 19 to 35; and
A is either

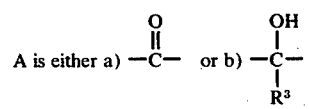

wherein $R^3$ is a hydrogen atom or alkyl having from 1 to 4 carbon atoms.

In the above-presented definitions of alkyl groups suitable as $R^1$, $R^2$ or $R^3$, it is to be understood that the alkyl portions may be methyl, ethyl, propyl or butyl, including isomers where such exist, e.g., t-butyl.

Compounds I, then consists of two classes of compounds, i.e., compounds Ia when A is of type a), i.e., carbonyl, and compounds Ib when A is of type b), i.e., a carbinol function.

Compounds Ia may be obtained by oxidizing (process a) in a suitable medium, a suitable pyridyl carbinol (a compound Ib in which $R^3$ is a hydrogen atom), i.e., a compound Ib':

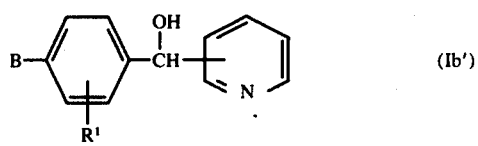

wherein $R^1$ is as defined above; and B is

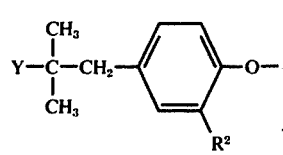

wherein

Y and $R^2$ are as defined above.

The oxidation of a compound Ib', (process a) may be accomplished in the conventional manner for oxidizing a secondary aliphatic alcohol function to a carbonyl function, e.g., by reacting a compound Ib', at a temperature of, e.g., from about 20° to 140° C., in the presence of activated manganese dioxide ($MnO_2$) in a suitable medium, i.e., an inert solvent such as dichloromethane, 1,2-dichloroethane, benzene, toluene, xylene or dioxane. Preferably the reaction is carried out at the reflux temperature of the solvent, which is preferably dichloromethane, i.e., $CH_2Cl_2$.

Compounds Ib may be obtained by condensing a Grignard agent of formula II:

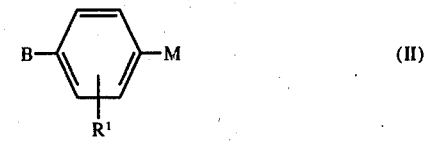

wherein

M is magnesium halide and $R^1$ and B are as defined above, with a suitable carbonyl compound (III), i.e., a pyridine carboxyaldehyde or a pyridyl ketone depending upon whether the $R^3$ is a hydrogen atom or alkyl;

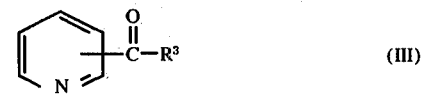

wherein $R^3$ is as defined above, in the presence of an aprotic solvent and under essentially anhydrous conditions, to obtain a corresponding Grignard adduct, which is then hydrolyzed to the corresponding compound Ib.

The preparation of a compound Ib (process b) is conveniently carried out in the manner, and under the conditions conventionally applied in carrying out the well-known Grignard reactions. Convenient temperatures are those of from about 0° to 70° C., preferably at the reflux temperature of the solvent. Suitable aprotic solvents are ethers, such as tetrahydrofuran and diethyl ether. Magnesium halides include magnesium bromide and iodide; magnesium bromide being preferred as M. It is particularly convenient to prepare a Grignard reagent in which M is a magnesium halide in situ, e.g., by reacting an aryl halide of formula IV:

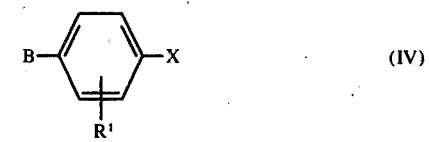

wherein $R^1$ and B are as defined above, and X is bromo or iodo, with magnesium metal at temperatures and in a solvent suitable for carrying out process b), under essentially anhydrous conditions. A small amount of solid iodine may be added to aid in initiating the reaction, as is commonly done in preparing Grignard reagents. Avoidance of moisture to achieve essentially anhydrous conditions is exercised, e.g., "dry" solvents and moisture-free apparatus being employed.

The hydrolysis of the resulting adduct may be carried out in the manner conventionally employed in hydrolyzing Grignard adducts, e.g., by treating the Grignard adduct with water, or an aqueous salt, acid or base, e.g., saturated ammonium chloride solution.

The products of the above-described reactions may be recovered and refined in conventional manner, e.g., by crystallization, distillation or chromatographic techniques, such as eluting from a chromatographic column or separating on a silica layer.

Starting materials and reagents used in the above-described reactions, e.g., compounds III and IV are either known and obtained by methods described in the literature, or where not known, may be obtained by methods analogous to those described in the literature. Some of the reactants and starting materials are commercially available.

The above-described reactions may conveniently be represented by the following reaction scheme wherein $R^1$, B, $R^3$, X and M are as defined above:

REACTION SCHEME

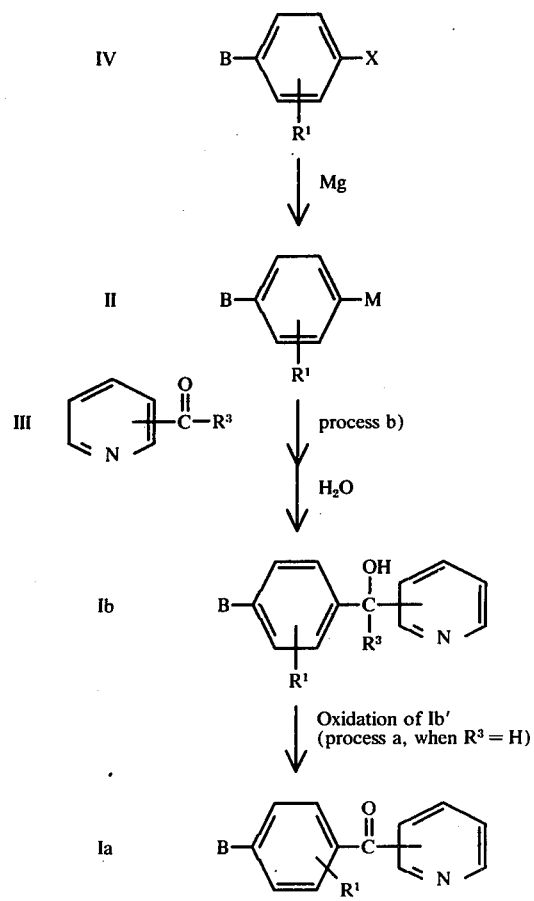

STATEMENT OF UTILITY

The compounds of formula I are useful because they possess pharmacological activities in animals. In particular, the compounds I are useful as hypolipidemic agents. The activity of compounds I as hypolipidemic agents, particularly hypolipoproteinemia agents, as evidenced, for example, by lowering cholesterol and triglyceride blood serum levels in tests on a group of white rats which are given typically, 10 to 250 milligrams per kilogram of body weight per diem of the compound orally, for 6 days, followed by extraction with isopropanol of serum or plasma after anesthetizing the rats with sodium hexobarbital, and then noting the cholesterol and triglyceride contents as compared to those of a control group. The cholesterol and triglyceride contents are determined by the methods described by Lofland, H. B., Anal. Biochem. 9: 393 (1964): (Technicon method N 24a): and G. Kessler and H. Lederer, Technicon Symposium, Mediad Inc., New York, pages 345–347 (1956), respectively. For such usage, the compounds may be administered orally or parenterally, preferably orally, and in admixture with conventional pharmaceutical carriers. The dosage administered may vary depending upon known variables such as the particular compound employed and the severity of the condition being treated. However, in general, satisfactory results are obtained when administered at a daily dosage of from about 4 milligrams to about 250 milligrams per kilogram of animal body weight, preferably given orally and in divided doses, 2 to 4 times a day, or in sustained release form. For large mammals the total daily dosage is from about 300 milligrams to about 3,000 milligrams of the compound, and the dosage forms suitable for internal administration comprise from about 75 to 1,500 milligrams of the compound in admixture with a solid or sterile liquid pharmacologically acceptable carrier or diluent.

The compounds of formula Ib are also useful as anti-obesity agents, as indicated by the glucose transport test carried out in Male Wistar rats dosed orally with from about 2 to 200 milligrams of test material per kilogram of animal body weight after at least 20 hours of fasting. One hour after receiving the drug, the animal is sacrificed and the upper small intestine is removed and washed with glucose-saline. A 5 cm section of the intestine is inverted so that the mucosal surface is on the outside. One end of the segment is tied off and the center of the sac, so formed, is filled with oxygen-saturated Kreb's bicarbonate buffer. The other end is then closed to form a sac and the sac is incubated in 10 ml of oxygen-saturated bicarbonate buffer for 60 minutes at 37° C. Both the outside and inside solutions contain initially 0.3% of glucose. At the end of the incubation time the glucose content of the outer (mucosal) and the inner (serosal) solution is determined using the standard Autoanalyzer procedure. Similar preparations are prepared simultaneously from animals receiving the vehicle only to serve as controls. The percentage inhibition of glucose transport caused by the drug is calculated from the formula $$\% I = 100 - \left( \frac{St - Mt}{Sc - Mc} \times 100 \right)$$

where
I equals inhibition
S equals glucose concentration (mg%) of serosal fluid at the end of an experiment
M equals glucose concentration (mg%) of mucosal fluid at the end of an experiment
c equals control animal t equals drug treated animal.

The anti-obesity effective dosage of compounds I employed in the alleviation of obesity will vary depending on the particular compound employed and the severity of the condition being treated. However, in general, satisfactory results are obtained when the compounds of formula I are orally administered at a daily dosage from about 2 to 200 milligrams per kilogram of animal body weight, preferably given in divided doses two to four times per day or in sustained release form. For most large mammals, the total daily dosage is from about 150 milligrams to about 1,500 milligrams. Dosage forms suitable for internal use comprise from about 37.5 to about 750 milligrams of active compound in admixture with a solid or sterile liquid pharmaceutically-acceptable carrier or diluent. In general, oral administration is preferred. Solid compositions, e.g., capsules and tablets, are most preferred.

For the above-described uses, as noted above, oral administration with carriers or diluents may take place in such conventional forms as tablets, dispersible powders, granules, capsules, syrups and elixirs. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents, such as calcium carbonate, sodium carbonate, lactose and talc, granulating and disintegrating agents, e.g., starch and alginic acid, binding agents, e.g., starch, gelatin and acacia and lubricating agents, e.g., magnesium stearate, stearic acid and talc. The tablets may be uncoated or coated by known techniques to delay disintegration and absorption in the gastro-intestinal tract and, thereby provide a sustained action over a longer period. Similarly, suspensions containing, for example, from about 0.5 to 5% of suspending agent, syrups containing, for example, from about 10 to 50% of sugar, and elixirs containing, for example, from about 20 to 50% of ethanol may contain the active ingredient in admixture with any of the conventional excipients utilized for the preparation of such compounds, e.g., suspending agents (methylcellulose, tragacanth and sodium alginate), wetting agents (lecithin, poloxyethylene stearate and polyoxyethylene sorbitan monooleate) and preservatives (e.g., ethyl-p-hydroxy-benzoate). Capsules preferably contain the active ingredient admixed with an inert diluent, e.g., a solid diluent such as calcium carbonate, calcium phosphate and kaolin or a liquid diluent, such as polyethylene glycol or an edible oil, e.g., peanut, corn or sesame oil. The preferred pharmaceutical compositions from the standpoint of preparation and ease of administration are orally administrable compositions, particularly tablets and solid or liquid diluent-filled capsules.

For the above-described uses, compounds I may be similarly administered in the form of their nontoxic pharmaceutically-acceptable acid addition salts. Such salts do not materially differ from the free base in their pharmacological effects and are included within the scope of the invention. The acid addition salts are readily prepared by reacting the base with pharmacologically acceptable acids in conventional manner. Representative of such salts are the mineral acid salts, such as the hydrochloride, hydrobromide, sulfate, phosphate and the like and the organic acid salts such as the benzoate, acetate, maleate, fumarate, p-toluenesulfonate, benzenesulfonate and the like.

Generally preferred compounds I are those in which Y is methyl, and more particularly, where each of $R^1$, $R^2$ and $R^3$ is a hydrogen atom. Of particular interest are the compounds of formula Ib as anti-obesity agents, especially those in which $R^3$ is hydrogen, i.e. the compounds Ib'.

In the following examples which illustrate the invention, temperatures are in degrees centigrade, and room temperature is 20° to 30° C.

EXAMPLE 1

1-[p-(4-neopentylphenoxy)phenyl]-1-(4-pyridyl)-methanol*

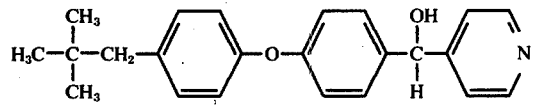

*may also be called p-[4'-(2,2-dimethylpropyl)-phenoxy]-phenyl-(4-pyridyl)-carbinol or 1-neopentyl-4-[α-hydroxy-α-(4-pyridyl)-p-tolyloxy]-benzene.

To form a Grignard reagent, to 3.6 g. of magnesium metal and a crystal of iodine are added, all at once, 25 ml. of a solution of 9.0 g. dibromoethane and 25.0 g. of p-(4-neopentylphenoxy)-bromobenzene in 150 ml. of absolute tetrahydrofuran (THF). After initiating the Grignard reaction, the rest of the above THF solution is added dropwise to maintain gentle reflux. The (Grignard reagent) reaction mixture is thereafter refluxed for half an hour; cooled and to it is added, dropwise, a solution of 8.3 g. of 4-pyridine-carboxaldehyde in 20 ml. of absolute THF. The reaction mixture is then stirred overnight, decomposed with saturated ammonium chloride aqueous solution and 100 ml. ether added. The organic phase is separated, dried over anhydrous sodium sulfate, filtered, and evaporated under vacuum to dryness to yield a residue. The residue is chromatographed on silica gel, first with toluene as the eluent and subsequently with toluene containing increasing concentrations of chloroform. The desired fractions are collected and evaporated under vacuum to dryness to yield a residue. From the residue is crystallized (from ether) the title product, m.p. 120°–122° C.

EXAMPLE 2

1-(4-pyridyl)-1-[p-(4-neopentylphenoxy)-phenyl]-ketone*

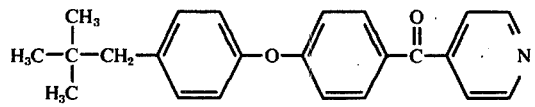

*may also be called p-(4-neopentylphenoxy)phenyl 4-pyridyl ketone.

A mixture of 6.0 g. of 1-[p-(4-neopentylphenoxy)-phenyl]-1-(4-pyridyl)-methanol and 5.0 g. activated $MnO_2$ is refluxed in 500 ml. dichloromethane for 12 hours. Thereafter the solution is filtered free of $MnO_2$ and evaporated under vacuum to dryness. From the residue is crystallized with pentane the title product, m.p. 130°–132° C.

EXAMPLE 3

Repeating the procedure of Example 1, but replacing the 4-pyridinecarboxaldehyde used therein with an approximately equal amount of:
a. 2-pyridinecarboxaldehyde or
b. 3-pyridinecarboxaldehyde; there is accordingly obtained:
   a.    1-[p-(4-neopentylphenoxy)phenyl]-1-(2-pyridyl)methanol; and
   b.    1-[p-(4-neopentylphenoxy)phenyl]-1-(3-pyridyl)methanol, respectively, which upon treatment as described in Example 2 yields:
   c. p-(4-neopentylphenoxy)phenyl 2-pyridyl ketone; and
   d. p-(4-neopentylphenoxy)phenyl 3-pyridyl ketone, respectively.

EXAMPLE 4

Repeating the procedure of Example 1, but using in place of the p-(4-neopentylphenoxy)-bromobenzene used therein, an approximately equivalent amount of:
   a. p-[4-(2,2-dimethylbutyl)phenoxy]bromobenzene; or
   b. p-[4-(2,2-dimethylpentyl)phenoxy]bromobenzene, there is accordingly obtained:
   a. 1-{p-[4-(2,2-dimethylbutyl)phenoxy]phenyl}-1-(4-pyridyl)-methanol; and
   b. 1-{p-[4-(2,2-dimethylpentyl)phenoxy]pentyl}-1-(4-pyridyl)-methanol, respectively.

EXAMPLE 5

1-{p-[(4-neopentylphenoxy)phenyl)]}-1-(4-pyridyl)-ethan-1-ol

Repeating the procedure of Example 1, but replacing the 4-pyridinecarboxaldehyde used therein with an approximately equivalent amount of 4-acetylpyridine, there is accordingly obtained the title product.

EXAMPLE 6

Capsules and tablets containing the ingredients indicated below may be prepared by conventional techniques and are useful in treating lipidemia, particularly hyperlipoproteinemia, in mammals at a dose of one capsule or tablet two to four times per day:

| Ingredient | Weight in Milligrams | | |
|---|---|---|---|
| | Tablet | Capsule | Capsule |
| 1-(4-pyridyl)-1-[p-(4-neopentylphenoxy)-phenyl]-ketone | 100 | 100 | 100 |
| Tragacanth | 10 | | |
| Lactose | 147.5 | 120 | |
| Corn Starch | 25 | | |
| Talcum | 15 | | |
| Magnesium Stearate | 2.5 | | |
| Polyethylene Glycol (M.W. 6000) | | | 230 |

EXAMPLE 7

Capsules and tablets containing the ingredients indicated below may be prepared by conventional techniques and are useful in treating obesity in mammals at a dose of one capsule or tablet two to four times per day:

| Ingredient | Weight in Milligrams | | |
|---|---|---|---|
| | Tablet | Capsule | Capsule |
| 1-[p-(4-neopentylphenoxy)-phenyl]-1-(4-pyridyl)-methanol | 50 | 50 | 50 |
| Tragacanth | 10 | | |
| Lactose | 197.5 | 170 | |
| Corn Starch | 25 | | |
| Talcum | 15 | | |
| Magnesium Stearate | 2.5 | | |
| Polyethylene Glycol (M.W. 6000) | | | 280 |

What is claimed is:

1. A compound which is a free base of the formula:

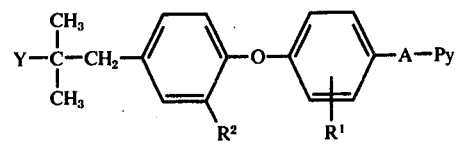

wherein
Y is unbranched alkyl having from 1 to 3 carbon atoms,
each of $R^1$ and $R^2$ is, independently, a hydrogen atom, alkyl having from 1 to 4 carbons, or a halogen atom having an atomic weight of from about 19 to 35; and

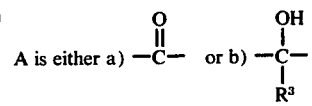

wherein
$R^3$ is a hydrogen atom or alkyl having from 1 to 4 carbon atoms; and
Py is a pyridyl radical which may be attached at its 2-, 3-, or 4-position; or
a pharmaceutically-acceptable acid addition salt thereof.

2. A compound of claim 1 in which A is of type a).
3. A compound of claim 2 in which $R^1$ is a hydrogen atom.
4. A compound of claim 3 in which $R^2$ is a hydrogen atom.
5. A compound of claim 2 in which Py is a 4-pyridyl radical.
6. A compound of claim 2 in which Py is a 2-pyridyl radical.
7. A compound of claim 2 in which Py is a 3-pyridyl radical.
8. The compound of claim 5 which is 1-(4-pyridyl)-1-[p-(4-neopentylphenoxy)-phenyl]-ketone.
9. A compound of claim 2 in which Y is methyl.
10. A compound of claim 2 in which A is of type b).
11. A compound of claim 10 in which $R^1$ is a hydrogen atom.
12. A compound of claim 11 in which $R^2$ is a hydrogen atom.
13. A compound of claim 10 in which Py is a 4-pyridyl radical.
14. A compound of claim 10 in which Py is a 2-pyridyl radical.
15. A compound of claim 10 in which Py is a 3-pyridyl radical.
16. A compound of claim 10 in which Y is methyl.
17. A compound of claim 10 in which $R^3$ is a hydrogen atom.
18. The compound of claim 17 which is 1-[p-(4-neopentylphenoxy)-phenyl]-1-(4-pyridyl-methanol.

* * * * *